(12) United States Patent
Quigley

(10) Patent No.: US 6,854,846 B2
(45) Date of Patent: Feb. 15, 2005

(54) FUNDUS PHOTOGRAPHIC TECHNIQUE TO DETERMINE EYE REFRACTION FOR OPTIC DISC SIZE CALCULATIONS

(76) Inventor: Michael Quigley, 396 Roslyn, Westmount, Quebec H3Z 2L6 (CA)

( * ) Notice: Subject to any disclaimer, the term of this patent is extended or adjusted under 35 U.S.C. 154(b) by 90 days.

(21) Appl. No.: 10/203,320
(22) PCT Filed: Feb. 8, 2001
(86) PCT No.: PCT/CA01/00142
§ 371 (c)(1), (2), (4) Date: Nov. 15, 2002
(87) PCT Pub. No.: WO01/58343
PCT Pub. Date: Aug. 16, 2001

(65) Prior Publication Data
US 2003/0133073 A1 Jul. 17, 2003

Related U.S. Application Data
(60) Provisional application No. 60/181,334, filed on Feb. 9, 2000.

(51) Int. Cl.$^7$ .............................................. A61B 3/14
(52) U.S. Cl. ....................................................... 351/206
(58) Field of Search ................................ 351/204–208, 351/216–218, 246

(56) References Cited

U.S. PATENT DOCUMENTS

| | | | |
|---|---|---|---|
| 4,265,518 A | | 5/1981 | Matsumura |
| 4,331,132 A | | 5/1982 | Mukasa |
| 4,372,655 A | * | 2/1983 | Matsumura et al. ........ 351/206 |
| 5,250,966 A | | 10/1993 | Oda et al. |
| 5,446,509 A | | 8/1995 | Okinishi |
| 5,830,147 A | | 11/1998 | Feke et al. |
| 5,867,249 A | | 2/1999 | Ichiki et al. |
| 5,871,439 A | | 2/1999 | Takahashi et al. |

FOREIGN PATENT DOCUMENTS

JP   59097276   6/1984

OTHER PUBLICATIONS

Bengtsson, Bo et al., Correction of optic disc measurements on fundus photographs, Graefe's Arch Clin. Esp Ophthalmol (1992)230:24–28.

Jonas, Jost B. et al., Ranking of Optic Disc Variables for Detection of Glaucomatous Optic Nerve Damage, Investigative Ophthalmology & Visual Science, Jun. 2000, vol. 41, No. 7, 1764–1773.

Bengtsson, Bo et al., Some essential optical features of the Zeiss fundus camera, Acta Ophthalmologica (1977) vol. 55. 123–131.

Chauhan, Balwantray, C., Confocal scanning laser tomography, Can J. Ophthalmol (1996) vol. 31, No. 3, 152–156.

Quigley, Michael G., A New Fundus Camera Technique to Help Calculate Eye–Camera Magnification, Arch Ophthalmol, May 2003, vol. 121, 707–709.

Heidelberg Retina Tomograph II, Operating Instructions book, Software Version 1.6, Revision 1.6–2E, May 2001, Heidelberg Engineering GmbH 2001, Germany.

The Heidelberg Retina Tomograph II brochure, Heidelberg Engineering GmbH, Germany, May 2001.

Phelps, Charles D. Glaucoma: General Concepts, Clinical Ophthalmology, vol. 3,Chap 42, pp 1–8, 1991.

Papastathopoulos, K.I. et al., Ophthalmoscopic assessment of the size of the optic nerve papilla, Klin Monatsbl Augenheilkd. Nov. 1997; 211(5):291–5.

Quigley, M.G., Visual Fields, Psychophysics, and Electrophysiology III Poster Presentation May 1, 2000, Hall A, IOVS, published abstract Mar. 15, 2000, vol. 41, No. 4, S290.

* cited by examiner

*Primary Examiner*—George Manuel
(74) *Attorney, Agent, or Firm*—Ogilvy Renault; James Anglehart

(57) ABSTRACT

The determination of magnification in an ophthalmic fundus camera image is achieved by detecting the focusing mechanism position, and using a calibration function to calculate the magnification from the focus position.

14 Claims, 1 Drawing Sheet

US 6,854,846 B2

FUNDUS PHOTOGRAPHIC TECHNIQUE TO DETERMINE EYE REFRACTION FOR OPTIC DISC SIZE CALCULATIONS

The present application claims the benefit of priority under 35USC§119(e) of U.S. patent application Ser. No. 60/181,334 filed Feb. 9, 2000.

FIELD OF THE INVENTION

The present invention relates generally to ophthamological retinal imaging, and in particular to a method and apparatus for determining an object size, such as the optic disc or other retinal object, in an image from a fundus camera.

BACKGROUND OF THE INVENTION

In ophthalmic imaging, the determination of scale is a challenge for the ophthalmologist using a fundus camera.

For example, the determination of the true size of the optic nerve head from its image on a fundus photograph is of great clinical importance in the diagnosis of glaucoma. As is well recognized in the art, glaucoma is a visually debilitating disease process resulting in damage to the nerve tissue of the optic nerve and having prevalence in the over 40 age group of about 1% (see Duane's Clinical Ophthalmology, Tasman W and Jaeger E editors, Vol. 3, Chapter 42, Glaucoma: general concepts).

The current methods for determining optic disc size include performing an ultrasound of the eye to determine the axial length or diameter of the eye and from this value calculating the image magnification. Another method uses the optical error of the eye to calculate image magnification. A further method includes measures of the curvature of the cornea in addition to optical error of the eye (front surface of the eye) to better refine the accuracy of the technique using the optical error accuracy in calculating the image magnification (see Bengtsson B and Krakau C. E. T. "Correction of optic disc measurements on fundus photographs", Graefe's Arch Clin Exp Ophthalmol, 1992; 230: 24–8). These techniques are tedious as they require photograph and supplemental testing either to determine the axial length of the eye or its optical error (glass refraction) or its optical error and the curvature of the cornea.

The diagnosis of glaucoma from a fundus photographic image is aided by knowing the true size of the optic nerve head and the true area of the nerve tissue visualized or detected on it (Jonas et al, Investigative Ophthalmology and Visual Science, 2000). As reported by Jonas et al., the vertical cup-to-disc ratio corrected for optic disc size, the total neuroretinal rim area, the rim-to-disc area ratio, and the cup-to-disc area ratio corrected for disc size are the most valuable optic disc variables for early detection of glaucomatous optic nerve damage. Correction for optic disc size is necessary for optic disc variables directly or indirectly derived from the optic cup. However, as alluded to above, not all eyes are the same in terms of their optical errors and sizes which results in differences in image magnification on the fundus photo. This means that to calculate true sizes of objects on the fundus photo, the methods described above must be employed. This can be impractical.

Papastathopoulos and Jonas have also reported on efforts to evaluate the optic disc size using a slit lamp (see "Ophthalmoscopic assessment of the size of the optic nerve papilla", *Ophthalmoskopische Abschatzung der Grosse der Papilla N. optici.*, Klin Monatsbl Augenheilkd 1997 Nov;211(5):291–5). While feasible, such measurement methods are cumbersome and not easily put into everyday practice.

There are other retinal structures in the fundus photograph which can also be measured in absolute units, and these structures include retinal blood vessels (both normal and abnormal), tumors, hemorrhages, and exudates, to name a few. Although absolute sizing of these structures from the fundus photograph is not, as of now, as diagnostically important as the sizing of the optic nerve head, the ability to perform this function could well lead to new disease diagnostic criteria.

SUMMARY OF THE INVENTION

It is a goal of the present invention to provide a simple means to perform the mentioned magnification calculation to permit the determination of true sizes of optic nerve and optic nerve structures in order to allow for rapid screening for glaucoma from a simple fundus photograph. Early diagnosis of glaucoma would decrease patient disability and hence have important socioeconomic benefits.

It is a goal of the present invention to provide an expedient method for a good approximation of the true sizes or dimensions of objects of interest as viewed on a fundus image.

It is a goal of the present invention to provide a method and apparatus for determining, in an easy and reliable manner, a scale of an image and thus an object size, such as the optic disc or other retinal object, in the image from a fundus camera.

It is a further goal of the present invention to provide a method and apparatus for controlling for inter-session eye-camera magnification variability by helping place a fundus camera in front of the eye.

According to the invention there is provided a method of ophthalmological imaging comprising the steps of positioning a patient's eye before a fundus imaging apparatus, adjusting a focus mechanism of the imaging apparatus to bring a retina of the eye into focus, recording a position setting parameter value of the focus mechanism as adjusted in the previous step, acquiring an image using the fundus imaging apparatus, determining a magnification of the image using the position setting parameter value and a calibration function established for the focus mechanism, and displaying the image with an indication of the magnification.

Preferably, the step of displaying comprises superposing a scale index marker on the image, and the step of adjusting comprises manually operating a focus mechanism to bring the retina into focus. Preferably, the step of displaying comprises displaying the image on a screen, and the step of displaying comprises printing the image.

The steps of recording, determining and displaying may be carried out automatically by electronic means.

The method may also further comprising steps of re-positioning the patient's eye before a fundus imaging apparatus at a time of later examination, setting a focus mechanism of the imaging apparatus to the setting parameter value, adjusting a position of the imaging apparatus to bring the retina of the eye into focus, acquiring a second image using the fundus imaging apparatus, and displaying the second image with an indication of the scale.

According to a further aspect of the invention, there is provided a method of obtaining at least one parameter useful in diagnosing glaucoma comprising the steps of positioning a patient's eye before a fundus imaging apparatus, adjusting a focus mechanism of the imaging apparatus to bring a retina of the eye into focus, recording a setting parameter value of the focus mechanism as adjusted in the previous step, acquiring an image using the fundus imaging apparatus, determining a scale of the image using the setting parameter value and a calibration function established for the focus mechanism, and measuring true dimensions of an optic nerve head and nerve tissue of the eye using the image and the scale, calculating at least one parameter indicative of glaucoma using the true dimensions.

The step of adjusting may comprise manually operating a focus mechanism to bring the retina into focus. The steps of recording, determining, measuring and calculating may be carried out automatically by electronic means.

The method preferably further comprises steps of re-positioning the patient's eye before a fundus imaging apparatus at a time of later examination, setting a focus mechanism of the imaging apparatus to the setting parameter value, adjusting a position of the imaging apparatus to bring the retina of the eye into focus, acquiring a second image using the fundus imaging apparatus, measuring true dimensions of an optic nerve head and nerve tissue of the eye using the second image and the scale, and recalculating at least one parameter indicative of glaucoma using the true dimensions from the second image.

According to another aspect of the invention, there is provided a fundus camera comprising a focus mechanism, and measuring means associated with the focus mechanism for measuring a position setting parameter of the focus mechanism.

The measuring means may comprise a vernier scale on the camera focusing control knob. The measuring means may also be electronic and provide a position setting parameter signal, and the camera may further comprise means for automatically determining a magnification of an image using the signal and a calibration function for the focus mechanism.

The camera may also further comprise an image storage means for storing the image, and an image displaying means for displaying the image with an indication of the magnification.

BRIEF DESCRIPTION OF THE DRAWING

In the sole drawing, there is illustrated schematically a fundus camera having a focus mechanism with a scale acquiring a retinal image of an eye, according to a preferred embodiment of the invention.

DETAILED DESCRIPTION OF THE PREFERRED EMBODIMENT

Figure 1:
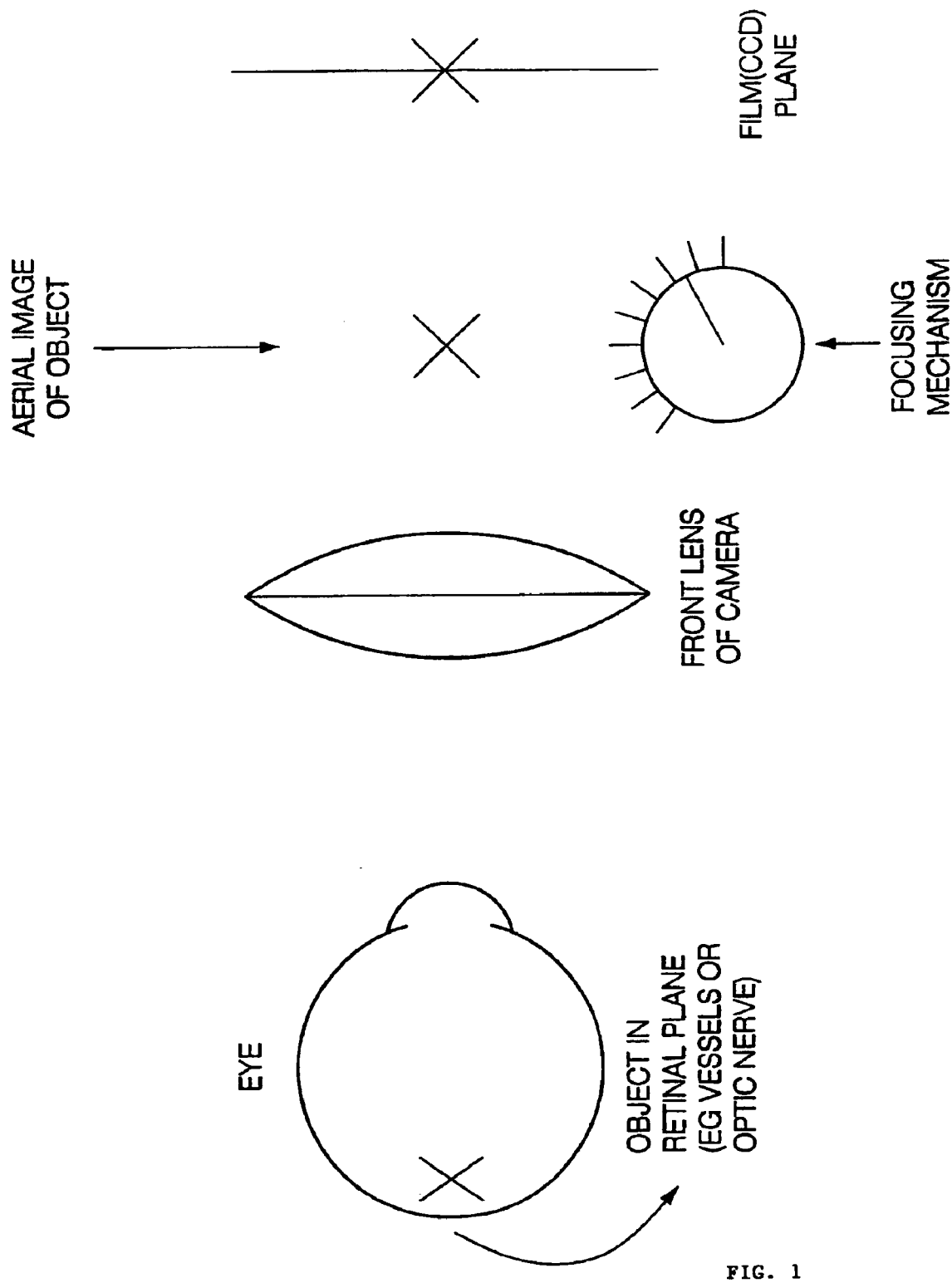

According to the invention, the position of the focusing knob or mechanism on the fundus camera is recorded, which position reflects the optical error or glass refraction of the eye. The glass refraction of the eye is used to calculate the object to image size ratio or magnification. This focus mechanism position is preferably automatically incorporated into a means to calculate the eye-camera magnification to arrive at a good estimate of the true or absolute measurements of retinal structures on the fundus photograph, such as the optic nerve, its components including the neuroretinal rim area and the cup. All of these measurements are important in the diagnosis of glaucoma.

The Applicant of the present application has noted that the observation and photography systems of the fundus camera rely on the principle of indirect ophthalmoscopy ("Some Essential Optical features of the Zeiss Fundus Camera", Bengtsson B and Krakau C. E. T. Acta Ophthalmologica Vol 55, 1977:123–131). The location of the intermediate real image of the fundus as created by the front lens of the camera depends on the optical power of the eye being photographed. The setting or position of the focusing mechanism on the camera to best see the intermediate image also reflects the glass refractive error of the eye. This measure of the glass refraction of the eye can then be used to calculate the eye-camera magnification factor produced on a fundus image. If, for example, the size of the optic disc is desired, this eye-camera magnification factor can be used along with the area of the disc occupied in the image (e.g. the area can be measured in pixels using image processing software, such as Adobe PhotoShop™) to arrive at an area measurement of the disc. This area measurement can then be corrected to yield a good approximation of the true disc area with "correction factors" (see Rudnicka et al. "Magnification Characteristics of Fundus Imaging Systems" Ophthalmology Vol 105, Number 12, December 1998; 2186–2192) or deriving "correction factors" from a standard group of subjects whose disc area has been determined by techniques as described above.

In tests performed, it has been found that the relation between focus mechanism position and glass refraction is highly correlated. Two telecentric fundus cameras—the Topcon TRC-50F50FT and the Topcon TRC-50x were used to perform twenty degree red free photographs of the optic nerve in twenty subjects (N=11 with the Topcon TRC-50F50FT and N=9 with the Topcon TRC-50x). A vernier scale was attached to the focussing knob which permitted a measurement of the knob position to be recorded. A correlation of this measurement with the eye refractive error was performed. The position of the focusing knob on both cameras correlated highly with the refractive error of the eye being photographed r=0.97 for the TRC-50F50FT and r=0.99 with the TRC50X. It should be noted that the photographs must be done in such a fashion so as to minimize the effect that the photographer's own lens accommodation may have on the focussing of the image. This can be done by having a photographer of sufficient age so his own diminished accommodative powers will not interfere with the focussing of the camera, or by ensuring that focussing the camera in done in such a way as to not employ one's own focussing ability. This problem will be not be important in cameras that employ an automatic or semi-automatic electronic focussing mechanism.

The position of the focussing mechanism reflects the optical refractive error of the eye being photographed which in turn can be used to calculate the eye-camera magnification. This position measurement can be incorporated into a simple method to calculate optic disc or other retinal object size. Although the above example was performed with telecentric cameras, some changes in this simple technique for retinal object size determination will also permit magnification factors for non-telecentric cameras to be calculated (Rudnicka et al. Magnification Characteristics of Fundus Imaging Systems. Ophthalmology Vol 105, Number 12, December 1998; 2186–2192).

Currently, the measurement of fundus (retinal) objects from a photographic image captured with a fundus camera is done by calculating manually the eye-camera magnification system with the formulas which employ either the length of the eye, the glasses strength of the eye, or the glasses strength and corneal curvature as mentioned above. Also known from the literature is that the known value of the glasses strength of the eye can be used to set the position of the focusing knob to bring the image of the retina into clear focus when taking the photograph of the retina, without adverse affect resulting from the photographer's own accommodation (see the mentioned Bengtsson and Krakau (1997), p. 131).

According to the present invention, the position of the focussing mechanism on the retinal camera is used directly to calculate the eye-camera magnification. This magnification factor can in turn also be used along with a simple software measuring tool whose scale changes according to the eye-camera magnification to calculate retinal object size (e.g. the optic nerve and the optic cup which are indices for diagnosing glaucoma, vessel caliber or tumor diameter). This is useful for rapid screening of large numbers of people especially with automation of photograph reading.

As will be appreciated, the method according to the invention may comprise the following steps as described herein below with reference to the appended drawing illustrating schematically a fundus optical imaging system.

The patient's eye is positioned for retinal photograph (or optic nerve). The aerial image of the object is focused on the film or CCD (image plane) with the focusing mechanism. The position of the focusing mechanism is recorded with the image. This can also be done by automatic means, such as a position sensor measuring the position of the focusing mechanism and a digital signal can be obtained for providing a focusing position measurement. The recorded position is then calibrated to the eye optical error (glass refraction) and is used to calculate the eye-camera magnification. An accurate scale of the fundus image can be determined using the eye-camera magnification calculated in the previous step.

When measuring objects found in the image using a software image analysis tool, the scale determined in the previous step is used to measure linear objects (e.g. vessel widths) or two-dimensional objects (e.g. the optic nerve head) in absolute units (e.g. In mm or $mm^2$). The position of the focusing mechanism recorded previously can be used in future photographs of the same patient to help control for inter-session eye-camera magnification variability by helping place the camera in front of the eye.

However, once the diagnosis of an ocular condition necessitating a fundus photograph is made (e.g. glaucoma) in a given patient, the eye-camera magnification is constant (unless of course the patient has had surgery to correct for myopia or cataract surgery or develops a condition such as a cataract which could change the glass refraction of the eye). As mentioned, the position of the focusing mechanism on the camera can be used to help minimize variability of magnification between photo sessions. For each session, the patient sits in front of the camera and the camera is manually moved to a fixed distance (say 10 cm) from the patient which is determined by the photographer. There is a certain error in this positioning owing to its manual input. This error can cause a change in the position of the focusing mechanism and hence a change in eye-camera magnification. Knowing the position of the focusing mechanism of the previous photographic session will permit a decrease in inter-session image magnification variability.

What is claimed is:

1. A method of ophthalmological imaging comprising the steps of:

positioning a patient's eye before a fundus imaging apparatus;

adjusting a focus mechanism of said imaging apparatus to bring a retina of said eye into focus;

recording a position setting parameter value of said focus mechanism as adjusted in the previous step;

acquiring an image using said fundus imaging apparatus;

determining the glass refraction of said patient's eye using said position setting parameter value and a calibration function established for said focus mechanism;

calculating a magnification from said glass refraction of said patient's eye; and displaying said image with an indication of said magnification.

2. The method as claimed in claim 1, wherein said step of displaying comprises superposing a scale index marker on said image.

3. The method as claimed in claim 1, wherein said step of adjusting comprises manually operating a focus mechanism to bring said retina into focus.

4. The method as claimed in claim 1, wherein said step of displaying comprises displaying said image on a screen.

5. The method as claimed in claim 1, wherein said step of displaying comprises printing said image.

6. The method as claimed in claim 1, wherein said steps of recording, determining and displaying are carried out automatically by electronic means.

7. The method as claimed in claim 1, further comprising steps of:

re-positioning said patient's eye before a fundus imaging apparatus at a time of later examination;

setting a focus mechanism of said imaging apparatus to said setting parameter value;

adjusting a position of said imaging apparatus to bring said retina of said eye into focus;

acquiring a second image using said fundus imaging apparatus; and displaying said second image with an indication of said magnification.

8. A method of determining the true dimensions of an optic nerve head and nerve tissue of a patient's eye, the method comprising the steps of:

positioning a patient's eye before a fundus imaging apparatus;

adjusting a focus mechanism of said imaging apparatus to bring a retina of said eye into focus;

recording a setting parameter value of said focus mechanism as adjusted in the previous step;

acquiring an image using said fundus imaging apparatus;

determining a glass refraction of said patient's eye using said setting parameter value and a calibration function established for said focus mechanism;

determining a scale of said image using said glass refraction of said patient's eye; and measuring true dimensions of an optic nerve head and nerve tissue of said eye using said image and said scale.

9. The method as claimed in claim 8, wherein said step of adjusting comprises manually operating a focus mechanism to bring said retina into focus.

10. The method as claimed in claim 8, wherein said steps of recording, determining, measuring and calculating are carried out automatically by electronic means.

11. The method as claimed in claim 8, further comprising steps of:

re-positioning said patient's eye before a fundus imaging apparatus at a time of later examination;

setting a focus mechanism of said imaging apparatus to said setting parameter value;

adjusting a position of said imaging apparatus to bring said retina of said eye into focus;

acquiring a second image using said fundus imaging apparatus;

measuring true dimensions of an optic nerve head and nerve tissue of said eye using said second image and said scale; and.

12. A fundus camera comprising:

a focus mechanism for focusing a fundus camera to image a retina;

measuring means associated with said focus mechanism for measuring a position setting parameter of said focus mechanism and providing a position setting parameter signal; and means for automatically determining the glass refraction of patient's eye of said image using said signal and a calibration function for said focus mechanism.

13. The camera as claimed in claimed in claim 12, wherein a magnification of said image is a function of said glass refraction of said patient's eye, further comprising:

an image storage means for storing said image; and an image displaying means for displaying said image with an indication of said magnification.

14. A method of calculating the glass refraction of a patient's eye, the method comprising the steps of:

positioning a patient's eye before a fundus imaging apparatus;

recording the separation distance between said patient's eye and said imaging apparatus;

adjusting a focus mechanism of said imaging apparatus to bring an image of a retina of said eye into focus;

recording a position setting parameter value of said focus mechanism as adjusted in the previous step; and calculating the glass refraction of said patient's eye using said separation distance and said position setting parameter value;

displaying said image.

* * * * *